US011324460B2

(12) United States Patent
Ogura et al.

(10) Patent No.: US 11,324,460 B2
(45) Date of Patent: May 10, 2022

(54) X-RAY MAMMOGRAPHY APPARATUS AND COMPUTER PROGRAM PRODUCT

(71) Applicant: Canon Medical Systems Corporation, Otawara (JP)

(72) Inventors: Tomoaki Ogura, Otawara (JP); Takehito Tomaru, Otawara (JP); Seiichirou Nagai, Otawara (JP); Yasushi Sakai, Kawasaki (JP); Yuuji Kuki, Utsunomiya (JP); Rie Ochiai, Nasushiobara (JP); Naoko Kuratomi, Sakura (JP); Takahiro Inagaki, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 0 days.

(21) Appl. No.: 16/430,750

(22) Filed: Jun. 4, 2019

(65) Prior Publication Data
US 2019/0374176 A1 Dec. 12, 2019

(30) Foreign Application Priority Data
Jun. 12, 2018 (JP) .............................. JP2018-112306

(51) Int. Cl.
*A61B 6/04* (2006.01)
*A61B 6/00* (2006.01)

(52) U.S. Cl.
CPC .............. *A61B 6/0414* (2013.01); *A61B 6/40* (2013.01); *A61B 6/42* (2013.01); *A61B 6/4452* (2013.01); *A61B 6/502* (2013.01); *A61B 6/54* (2013.01)

(58) Field of Classification Search
CPC ........... A61B 6/0414; A61B 6/40; A61B 6/42; A61B 6/4452; A61B 6/502; A61B 6/54
See application file for complete search history.

(56) References Cited

U.S. PATENT DOCUMENTS 5,590,166 A * 12/1996 Suni ..................... A61B 6/0414
378/196
9,826,950 B2 * 11/2017 Den Heeten ........... A61B 6/502
(Continued)

FOREIGN PATENT DOCUMENTS

JP 2009-291477 A 12/2009
JP 2012-045022 A 3/2012
(Continued)

OTHER PUBLICATIONS

Japanese Office Action dated Mar. 22, 2022, issued in Japanese Patent Application No. 2018-112306 (including translation from Global Dossier).

*Primary Examiner* — Dani Fox
*Assistant Examiner* — Soorena Kefayati
(74) *Attorney, Agent, or Firm* — Oblon, McClelland, Maier & Neustadt, L.L.P.

(57) ABSTRACT

According to one embodiment, an X-ray mammography apparatus includes a breast support, a compression plate, and a compression controller. The breast support where the breast is placed. The compression plate is arranged such that the breast is sandwiched between the breast support and the compression plate. The compression controller is configured to control the breast support to move toward the compression plate so as to compress the breast from below between the breast support and the compression plate.

14 Claims, 4 Drawing Sheets

(56) References Cited

U.S. PATENT DOCUMENTS

| | | | | |
|---|---|---|---|---|
| 10,856,831 B2* | 12/2020 | Moon | | A61B 6/467 |
| 2003/0006387 A1* | 1/2003 | Marie | | A61B 6/502 |
| | | | | 250/581 |
| 2004/0131145 A1* | 7/2004 | Ohara | | A61B 6/544 |
| | | | | 378/37 |
| 2005/0063509 A1* | 3/2005 | Defreitas | | A61B 6/4233 |
| | | | | 378/37 |
| 2006/0245541 A1* | 11/2006 | Aubel | | A61B 6/0414 |
| | | | | 378/37 |
| 2009/0103796 A1* | 4/2009 | Akagi | | A61B 6/4494 |
| | | | | 382/132 |
| 2009/0268864 A1* | 10/2009 | Nishida | | A61B 6/502 |
| | | | | 378/37 |
| 2009/0304146 A1* | 12/2009 | Ramsauer | | A61B 6/502 |
| | | | | 378/37 |
| 2012/0051501 A1* | 3/2012 | Nakayama | | A61B 6/022 |
| | | | | 378/37 |
| 2014/0219548 A1* | 8/2014 | Wels | | A61B 6/025 |
| | | | | 382/154 |
| 2014/0328458 A1* | 11/2014 | Erhard | | A61B 6/548 |
| | | | | 378/37 |
| 2015/0023476 A1* | 1/2015 | Muller | | A61B 6/0414 |
| | | | | 378/208 |
| 2015/0097127 A1* | 4/2015 | Kuwabara | | A61B 6/025 |
| | | | | 250/580 |
| 2015/0190105 A1* | 7/2015 | Sugahara | | G06T 7/0014 |
| | | | | 378/20 |
| 2015/0282770 A1* | 10/2015 | Klanian | | A61B 6/04 |
| | | | | 378/208 |
| 2016/0183889 A1* | 6/2016 | Matsuura | | A61B 6/502 |
| | | | | 378/37 |
| 2016/0206229 A1* | 7/2016 | Arai | | A61B 6/025 |
| 2016/0235379 A1* | 8/2016 | Homann | | A61B 6/502 |
| 2017/0000449 A1* | 1/2017 | Tsujii | | A61B 6/502 |
| 2017/0340303 A1* | 11/2017 | Stango | | A61B 6/4435 |
| 2017/0367674 A1* | 12/2017 | Arai | | A61B 6/42 |
| 2018/0184999 A1* | 7/2018 | Davis | | A61B 8/4416 |
| 2018/0220986 A1* | 8/2018 | Choi | | A61B 6/4452 |
| 2018/0360403 A1* | 12/2018 | Muller | | A61B 6/42 |
| 2019/0090828 A1* | 3/2019 | Dederichs | | A61B 6/502 |
| 2019/0090833 A1* | 3/2019 | Koike | | G06K 9/6277 |
| 2019/0159741 A1* | 5/2019 | Fredenberg | | A61B 6/032 |

FOREIGN PATENT DOCUMENTS

| | | |
|---|---|---|
| JP | 2012-170718 | 9/2012 |
| JP | 2017-012409 A | 1/2017 |
| JP | 2017-225635 A | 12/2017 |

\* cited by examiner

X-RAY MAMMOGRAPHY APPARATUS AND COMPUTER PROGRAM PRODUCT

CROSS-REFERENCE TO RELATED APPLICATION

This application is based upon and claims the benefit of priority from Japanese Patent Application No. 2018-112306, filed on Jun. 12, 2018; the entire contents of which are incorporated herein by reference.

FIELD

Embodiments described herein relate generally to an X-ray mammography apparatus and a computer program product.

BACKGROUND

The mammography apparatus may be cited as an example of X-ray imaging apparatuses for capturing breast images of a subject. The mammography apparatus uses X-rays to create breast images of a subject, which are used to screen for the presence of a lesion such as a tumor, a mass, or breast cancer in the breast. When breast radiograph is performed, subject's breast is supported on a breast support and compressed by a compression plate such that the breast is thinly spread and less mammary glands overlap in the breast. The compression plate is configured to be movable through a C-arm, and is moved in parallel to the breast support side to thereby compress the breast.

Directions to compress the breast include the vertical direction. During the compression, the C-arm compresses the breast in the upright state (the breast support is on the lower side, the compression plate is on the upper side). In the upright compression, the breast support supports the breast, and the compression plate compresses the breast while moving down to the breast support. In this case, if the subject has small breasts, or the subject is a male, it is difficult to compress the breast.

DETAILED DESCRIPTION

Figure 1:
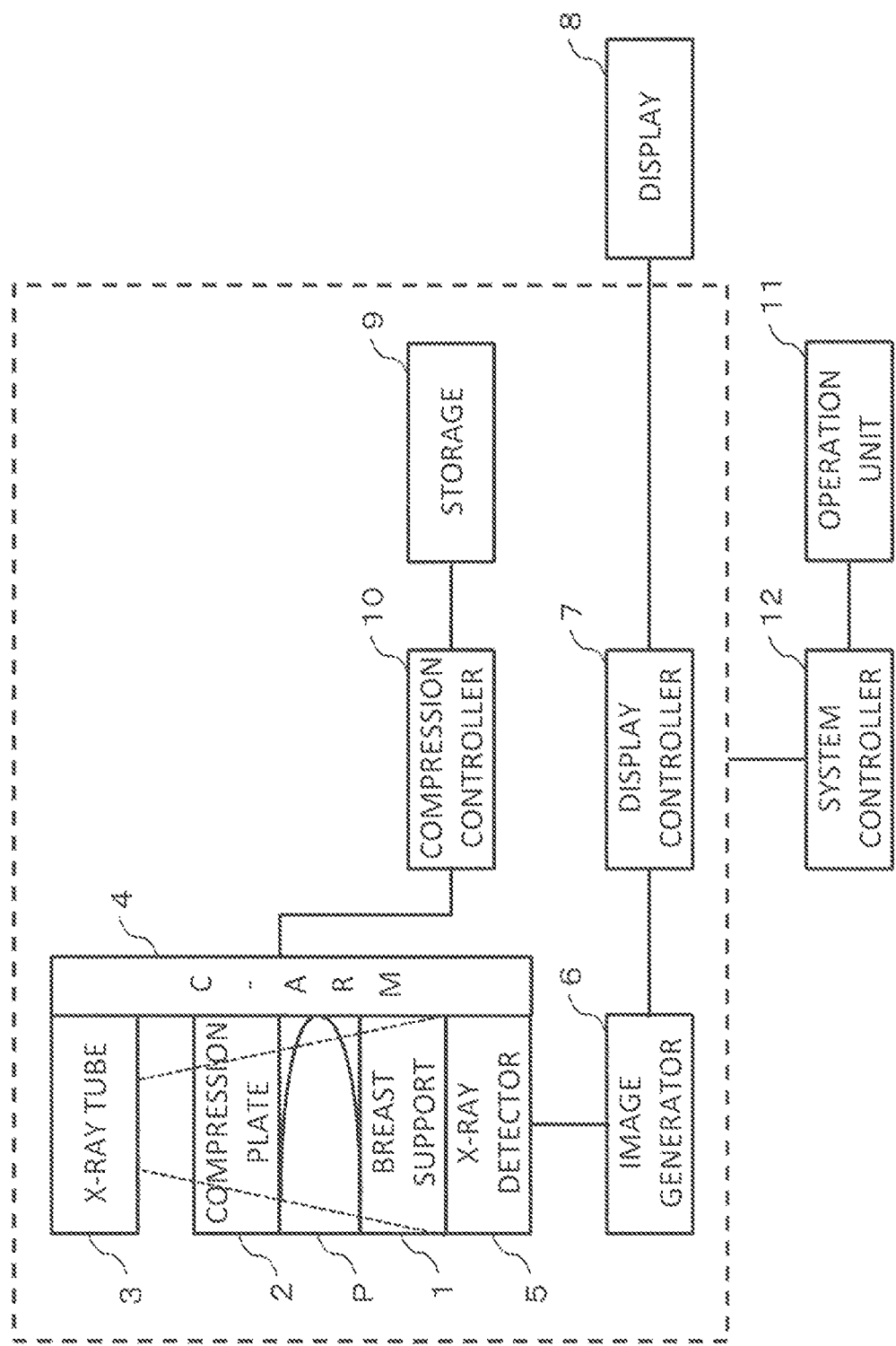
FIG. 1 is a block diagram illustrating the configuration of an X-ray mammography apparatus according to an embodiment.

In general, according to one embodiment, an X-ray mammography apparatus includes a breast support, a compression plate, and a compression controller. The breast support is arranged such that a breast is placed thereon. The compression plate is arranged such that the breast is sandwiched between the breast support and the compression plate. The compression controller is configured to control the breast support to move toward the compression plate so as to compress the breast from below between the breast support and the compression plate.

Referring now to the drawings, illustrative embodiments are described in detail.

FIG. 1 is a block diagram illustrating the configuration of an X-ray mammography apparatus according to an embodiment. The X-ray mammography apparatus of the embodiment includes a breast support 1, a compression plate 2, an X-ray tube 3, a C-arm 4, an X-ray detector 5, an image generator 6, a display controller 7, a display 8, a storage 9, a compression controller 10, an operation unit 11, and a system controller 12.

The breast support 1 supports a breast P placed thereon. The X-ray detector 5 is located below the breast support 1.

The compression plate 2 is arranged to face the breast support 1. The compression plate 2 is configured to be movable relative to the breast support 1 in parallel in a direction toward or away from the breast support 1, thereby compressing the breast P.

The X-ray tube 3 generates X-rays and emits the X-rays to the breast P. The C-arm 4 supports the breast support 1, the compression plate 2, the X-ray tube 3, and the X-ray detector 5. The compression plate 2 moves in parallel along the C-arm 4, thereby coming close to or away from relative to the breast support 1. An existing motor or rail may be used as this movement mechanism. The C-arm 4 and the breast support 1 are fixed to each other.

The X-ray detector 5 detects incident X-rays. The X-rays include those transmitted through the breast P. For example, the X-ray detector 5 is formed of a direct or indirect conversion flat-panel detector. The flat panel detector converts the incident X-rays into an electrical signal, and outputs it to the image generator 6.

The image generator 6 generates a mammography image of the breast P. Having received the electrical signal from the X-ray detector 5, the image generator 6 converts the signal from analog to digital. The image generator 6 generates a mammography image based on a digital signal obtained by the A/D conversion. The image generator 6 outputs the mammography image to the display controller 7.

The display controller 7 displays the mammography image on the display 8. The display 8 is formed of a display device such as a liquid crystal display (LCD) or an organic electroluminescence (EL) display.

The storage 9 is a memory configured to store medical record information of a subject. The medical record information indicates at least one of the gender, height, and screening history of the subject. The medical record information may be manually entered by the operator or may be entered by communication processing via an existing hospital information system. As an example of the hospital information system may be cited a system that can use the DICOM (Digital Imaging and Communications in Medicine) standard.

The compression controller 10 is a processor configured to control the breast support 1 to move relative to the position of the compression plate 2 based on position information indicating the positions of the breast support 1 and the compression plate 2. The breast P is compressed under the control of the compression controller 10 (described later in detail).

The operation unit 11 is operated by an operator such as a doctor or an engineer, and sends a signal or information corresponding to the operation to each part of the apparatus. The operation unit 11 is formed of operation devices such as a keyboard, a mouse, and a trackball. The operation unit 11 also includes a foot switch. At the time of breast compression, in general, the operator carefully operates the operation unit 11 while checking the compressed state of the breast.

The operator carries out the compression little by little while stepping on the foot switch. When the foot switch is being pressed, the compression plate 2 moves toward the breast support 1.

In the conventional operation, when the operator is stepping on the foot switch, the compression plate 2 moves toward the breast support 1 whose position is fixed. This is referred to as a first operation mode. The first operation mode can be switched to the second operation mode, in which, when the operator is stepping on the foot switch, the breast support 1 is moved toward the compression plate 2 whose position is fixed, in response to a predetermined switching operation on the operation unit 11. The switching operation may be appropriately set in the operation unit 11. For example, the switching operation may be set such that the operation mode is switched to the second operation mode when the foot switch (the operation unit 11) is stepped on a plurality of times continuously.

The system controller 12 controls the operation of each unit of the X-ray mammography apparatus. For example, the system controller 12 stores a computer program for implementing the functions of each unit of the X-ray mammography apparatus. The system controller 12 implements the above functions by executing this computer program. For example, the system controller 12 stores and executes a computer program that realizes the following operation.

Figure 2:
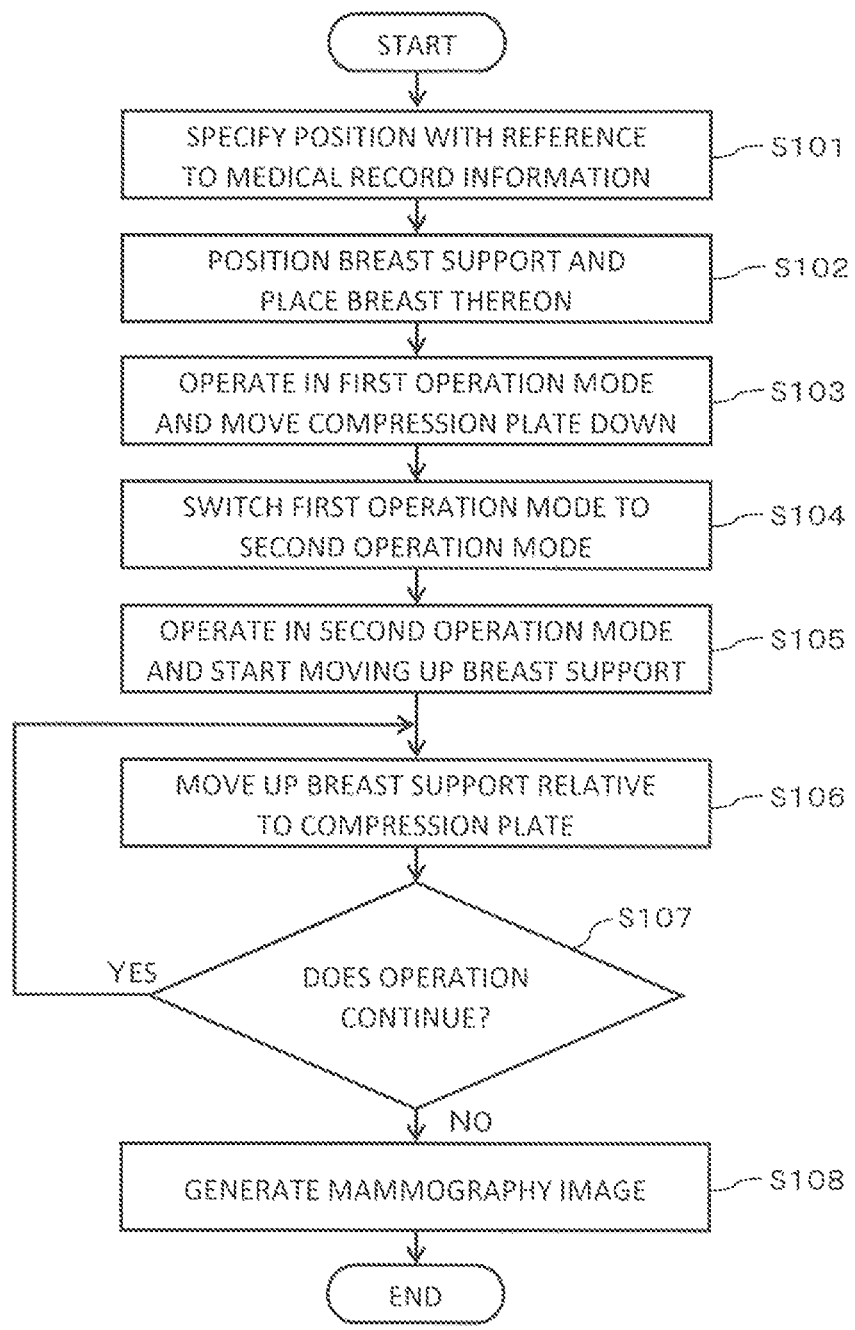
FIG. 2 is a flowchart illustrating the operation of the X-ray mammography apparatus according to the embodiment.

FIG. 2 is a flowchart illustrating the operation of the X-ray mammography apparatus according to the embodiment. As an initial setting of the operation, the X-ray mammography apparatus of the embodiment is set to the first operation mode, and the C-arm is set to the upright state.

Step S101: With reference to the medical record information of the subject, the compression controller 10 specifies the position to which the lower edge of the breast P and the upper surface of the breast support 1 are positioned. For example, when the medical record information includes mammography screening history, the compression controller 10 specifies the position used in the past mammography screening as the position for the positioning. Alternatively, based on the position used in the past mammography screening, the compression controller 10 specifies a position below that position (for example, a position at a predetermined distance below that position).

If the medical record information does not include the screening history but does include the height, the compression controller 10 specifies a clinical standard value corresponding to the height for the positioning. For example, the storage 9 stores a table in which a clinical standard value is assigned to each height. The compression controller 10 reads out a standard value corresponding to the height of the subject to mammography, and sets it as the position for the positioning.

When the medical record information does not include the screening history and the height but includes the gender, the compression controller 10 specifies a clinical standard value corresponding to the gender for the positioning. For example, the storage 9 stores a table in which a clinical standard value is assigned to each gender. The compression controller 10 reads out a standard value corresponding to the gender of the subject to mammography, and sets it as the position for the positioning.

Step S102: The compression controller 10 moves the C-arm 4 in parallel in the vertical direction to the specified position, thereby positioning the upper surface of the breast support 1 with respect to the lower edge of the breast P. With this, the breast P is placed on the upper surface of the breast support 1. Thus, the breast P is supported by the breast support 1 (supporting step).

Figure 3:
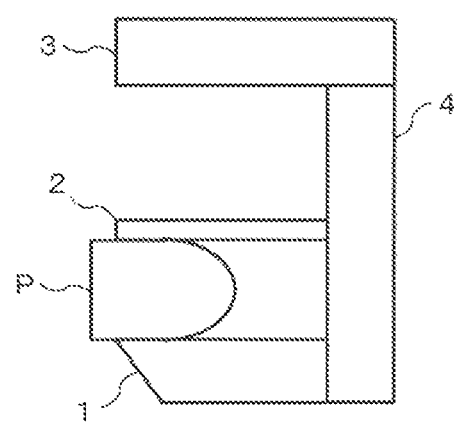
FIG. 3 is a schematic diagram illustrating a state after a first operation mode of the embodiment.

Step S103: In response to the operation of the operator stepping on the foot switch (the operation unit 11), the compression controller 10 moves the compression plate 2 (down) toward the breast support 1 while fixing the position of the breast support 1. As the compression plate 2 moves down, the lower surface of the compression plate 2 reaches the upper edge of the breast P. The operator appropriately releases the foot switch. The compression controller 10 stops moving down the compression plate 2 according to this operation. FIG. 3 is a schematic diagram illustrating a state after the first operation mode of the embodiment. In this state, the breast P is yet to be sufficiently compressed so as to be suitable for mammography. In the following steps, the breast P is further compressed.

Step S104: The first operation mode is switched to the second operation mode in response to the switching operation by the operator.

Step S105: In response to the operation of the operator stepping on the foot switch (the operation unit 11), the compression controller starts controlling the breast support 1 to move toward the compression plate 2 while fixing the position of the compression plate 2 (start of upward movement).

Figure 4:
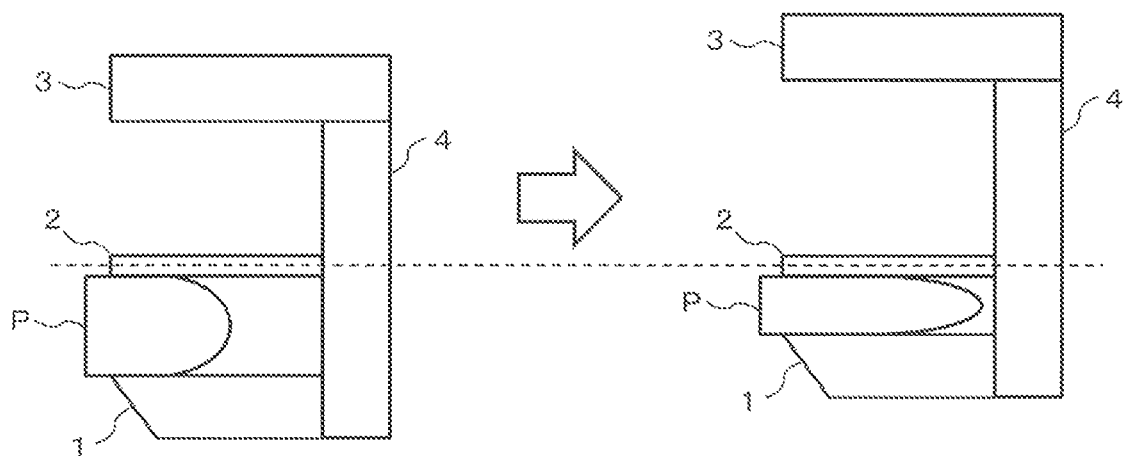
FIG. 4 is a schematic diagram illustrating an outline of breast compression by a second operation mode of the embodiment.

Step S106: The compression controller 10 moves the C-arm 4 up while fixing the position of the compression plate 2. FIG. 4 is a schematic diagram illustrating an outline of breast compression by the second operation mode of the embodiment. At this time, the compression controller 10 moves down the compression plate 2 relative to the C-arm 4 and also moves up the C-arm 4 at the same speed as the moving down compression plate 2 (step S106: compression step). As a result, the C-arm 4 moves up relative to the compression plate 2 while the position of the compression plate 2 is fixed. As described above, the breast support 1 and the C-arm 4 are fixed to each other, and therefore the breast support 1 also moves up together with the C-arm 4. Since the position of the compression plate 2 is fixed, the distance between the breast support 1 and the compression plate 2 becomes shorter as the breast support 1 moves up, and the breast P is compressed.

Step S107: While the operator continues operating the foot switch (the operation unit 11), step S106 is repeated.

Step S108: After the operation in the second operation mode is completed, a mammography image is generated based on an existing mammography screening process.

The configuration and operation of the X-ray mammography apparatus according to the embodiment have been described above.

With a conventional X-ray mammography apparatus, for example, when the subject has very small breasts or the subject is a male, the C arm is rotated 180 degrees so as to be inverted (the breast support is on the upper side, the compression plate is on the lower side). Then, the compression plate is moved up toward the breast support to compress the breast. If the compression is performed in the inverted state, the breast can be compressed while the skin tissue of the abdomen of the subject is being stretched. Therefore, when screening is performed on a subject who has very small breasts or who is a male, the breast is compressed in such inverted state. However, this requires the C-arm to have a mechanism capable of achieving the inverted state, and causes additional work of rotating the C-arm 180 degrees, resulting in more trouble in screening.

On the other hand, with the X-ray mammography apparatus of the embodiment, the breast can be compressed from below while the C-arm is in the upright state. In other words, the breast compression can be performed without rotating the C-arm 180 degrees. Therefore, even when the subject has very small breasts or the subject is a male, the breast can be compressed without increasing trouble in screening.

Besides, when the breast is compressed in the inverted state, the compression plate moves up while supporting the breast. As a result, the positions of the breast and the breast support are more likely to shift than in the upright state, which makes it difficult to position the breast support relative to the breast.

On the other hand, with the X-ray mammography apparatus of the embodiment, compression in the second operation mode is started after the upper surface of the breast support contacts the lower edge of the breast and the lower surface of the compression plate contacts the upper edge of the breast. Accordingly, the position of the breast is less likely to shift during the compression, which facilitates the positioning of the breast support relative to the breast.

The term "processor" as used herein refers to a circuit such as, for example, a central processing unit (CPU), an application specific integrated circuit (ASIC), a programmable logic device including a simple programmable logic device (SPLD) and a complex programmable logic device (CPLD), a field programmable gate array (FPGA), or the like.

The processor reads out a program stored in the memory circuit and executes it, thereby realizing the functions. The program need not necessarily be stored in the memory circuit but may be directly incorporated in the circuit of the processor. In this case, the processor reads out the program incorporated in the circuit and executes it to realize the functions. Each processor of the embodiment need not necessarily be configured as a single circuit, but a plurality of independent circuits may be combined to form a single processor to realize the functions. Further, a plurality of constituent elements of the embodiment may be integrated into one processor to realize the functions.

According to at least one embodiment described above, breast compression can be performed easily even when the subject has very small breasts or the subject is a male.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray mammography apparatus, comprising:
a breast support where a breast is placed;
a compression plate arranged such that the breast is sandwiched between the breast support and the compression plate;
an arm (a) configured to (a1) support the breast support such that the breast support is fixed to the arm and (a2) support the compression plate such that the compression plate is movable relative to the fixed breast support, and (b) configured to be movable in a direction in which the breast support comes close to or goes away from the compression plate; and processing circuitry configured to
move the compression plate down toward the breast support, while maintaining a height of the breast support, until the compression plate reaches an upper edge of the breast that is placed on the breast support by moving the compression plate down relative to the arm, while keeping positions of the arm and the breast support fixed, and
move the breast support up toward the compression plate, while maintaining a height of the compression plate, so as to compress the breast-between the breast support and the compression plate after the compression plate reaches the upper edge of the breast by moving the compression plate down relative to the arm as the arm and the breast support move up so as to maintain the height of the compression plate.

2. The X-ray mammography apparatus of claim 1, wherein the processing circuitry is further configured to control the breast support to compress the breast without changing a relative height of the compression plate with respect to the breast.

3. The X-ray mammography apparatus of claim 1, further comprising:
an X-ray tube configured to emit X-rays; and
an X-ray detector configured to detect the X-rays, wherein the X-ray detector is arranged integrally with the breast support, and
the processing circuitry is further configured to move the X-ray detector together with the breast support toward the compression plate.

4. The X-ray mammography apparatus of claim 1, wherein the processing circuitry is further configured to move the breast support based on information related to a subject.

5. The X-ray mammography apparatus of claim 1, wherein the processing circuitry is further configured to move the arm up and move the compression plate down at a same speed.

6. The X-ray mammography apparatus of claim 4, wherein
the information indicates at least one of gender, height, and screening history of the subject, and
the processing circuitry is further configured to move the breast support based on the information.

7. The X-ray mammography apparatus of claim 6, wherein, when the information indicates the screening history, the processing circuitry moves the breast support by using information related to position of the breast support included in the screening history.

8. The X-ray mammography apparatus of claim 6, wherein when the information does not indicate the screening history, the processing circuitry moves the breast support by using information related to either one of the gender or the height of the subject.

9. A computer program product comprising a non-transitory computer-usable medium having computer-readable program codes that, when executed, cause a computer to:
move a compression plate down toward a breast support where a breast is placed, while maintaining a height of the breast support, by moving the compression plate down relative to the arm, while keeping positions of the arm and the breast support fixed until the compression plate reaches an upper edge of the breast that is placed on the breast support; and
move the breast support up toward the compression plate arranged such that the breast is sandwiched between the breast support and the compression plate, while maintaining a height of the compression plate, so as to compress the breast between the breast support and the compression plate after the compression plate reaches the upper edge of the breast by moving the compression plate down relative to the arm as the arm and the breast support move up so as to maintain the height of the compression plate, wherein the breast support and the compression plate are supported by an arm such that the breast support is fixed to the arm and the compression plate is movable relative to the fixed breast support, and the arm is movable in a direction in which the breast support comes close to or goes away from the compression plate.

10. The computer program product as claimed in claim 9, further comprising computer-readable program codes that further cause the computer to control the breast support to compress the breast without changing a relative height of the compression plate with respect to the breast.

11. The computer program product as claimed in claim 9, comprising computer-readable program codes that further cause the computer to move the breast support based on information related to a subject.

12. The computer program product as claimed in claim 11, wherein the information indicates at least one of gender, height, and screening history of the subject, and wherein the computer program product comprises computer-readable program codes that further cause the computer to move the breast support based on the information.

13. The computer program product as claimed in claim 12, wherein, when the information indicates the screening history, the computer-readable program codes further cause the computer to move the breast support by using information related to position of the breast support included in the screening history.

14. The computer program product as claimed in claim 12, wherein when the information does not indicate the screening history, the computer-readable program codes further cause the computer to move the breast support by using information related to either one of the gender or the height of the subject.

* * * * *